United States Patent [19]

Milder et al.

[11] Patent Number: 5,759,564
[45] Date of Patent: *Jun. 2, 1998

[54] IONTOPHORETIC MATERIAL

[75] Inventors: Frederic L. Milder, Brookline; Donald Anderson, Medfield; Barry D. Weitzner, Acton, all of Mass.

[73] Assignee: Implemed, Inc., Watertown, Mass.

[*] Notice: The term of this patent shall not extend beyond the expiration date of Pat. No. 5,741,224.

[21] Appl. No.: 633,222

[22] Filed: Apr. 16, 1996

[51] Int. Cl.$^6$ .................. A61F 2/02; A61N 1/30
[52] U.S. Cl. ............... 424/426; 424/449; 604/20
[58] Field of Search .................. 424/423, 449, 424/426; 604/20

[56] References Cited

U.S. PATENT DOCUMENTS

| | | | |
|---|---|---|---|
| 3,659,588 | 5/1972 | Kahn et al. | 128/2 R |
| 3,964,477 | 6/1976 | Ellis et al. | 128/172.1 |
| 4,027,393 | 6/1977 | Ellis et al. | 32/10 A |
| 4,054,139 | 10/1977 | Crossley | 128/260 |
| 4,126,937 | 11/1978 | Ellis et al. | 32/15 |
| 4,308,859 | 1/1982 | Child | 128/1 R |
| 4,313,438 | 2/1982 | Greatbatch | 128/207.21 |
| 4,411,648 | 10/1983 | Davis et al. | 604/21 |
| 4,474,570 | 10/1984 | Ariura et al. | 604/20 |
| 4,476,590 | 10/1984 | Scales et al. | 3/1.91 |
| 4,483,688 | 11/1984 | Akiyama | 604/265 |
| 4,564,361 | 1/1986 | Akiyama | 604/265 |
| 4,569,673 | 2/1986 | Tesi | 604/20 |
| 4,603,152 | 7/1986 | Laurin et al. | 604/265 |
| 4,886,075 | 12/1989 | Jones | 128/787 |
| 4,886,505 | 12/1989 | Haynes et al. | 604/265 |
| 5,049,140 | 9/1991 | Brenner et al. | 604/266 |
| 5,057,072 | 10/1991 | Phipps | 604/20 |
| 5,084,006 | 1/1992 | Lew et al. | 604/205 |
| 5,154,165 | 10/1992 | Elliott et al. | 128/419 |
| 5,302,172 | 4/1994 | Sage, Jr. et al. | 604/20 |
| 5,324,275 | 6/1994 | Raad et al. | 604/265 |
| 5,328,451 | 7/1994 | Davis et al. | 604/20 |
| 5,421,982 | 6/1995 | Ikeda et al. | 204/414 |
| 5,607,691 | 3/1997 | Hale et al. | 424/449 |

FOREIGN PATENT DOCUMENTS

| | | |
|---|---|---|
| 0206024 | 12/1986 | European Pat. Off. . |
| 3830359 | 12/1989 | Germany . |
| 0000890 | 3/1880 | United Kingdom . |
| WO1582016 | 12/1980 | WIPO . |
| WO9116946 | 11/1991 | WIPO . |

OTHER PUBLICATIONS

"Antibacterial Effects of Silver Electrodes with Weak Direct Current" *Antimicrobial Agents and Chemotherapy* vol. 6, No. 5. J.A. Spadaro et al., Nov. 1974, pp. 637–642.

"Electrical Conductivity", David Bloor, Queen Mary College, London, UK, Comprehensive Polymer Science, *The Synthesis, Characterization, Reactions & Applications of Polymers*, vol. 2 Polymer Properties.

Electrode and Bacterial Survival with Iontophoresis in Synthetic Urine, *The Journal of Urology*, vol. 147, May 1992, pp. 1310–1313.

Primary Examiner—Carlos Azpuru
Attorney, Agent, or Firm—Nutter, McClennen & Fish, LLP

[57] ABSTRACT

An iontophoretic material is provided that uses controlled electrical current derived from two dissimilar galvanic materials to drive oligodynamic metal ions into solution to kill microorganisms on and near the material. Iontophoretic structures or material associated with a medical device are partially or completely covered with one or more covering layers that alter physical, mechanical, chemical, or biological properties of the device and/or the iontophoretic material. In addition to being partially coated or completely enveloped by iontophoretic material or structures, all or a portion of a medical device can be integrated with, impregnated by, or fabricated from an iontophoretic material.

25 Claims, 4 Drawing Sheets

IONTOPHORETIC MATERIAL

FIELD OF THE INVENTION

The invention relates to oligodynamic iontophoresis, and more particularly to a structure for medical devices that reduces or eliminates infection by killing microorganisms with controlled oligodynamic iontophoresis.

BACKGROUND OF THE INVENTION

Oligodynamic metals, such as silver, are effective in minute quantities as bacteriostats and bactericides. The most active form of these oligodynamic metals is as ions in solution. While the precise nature of the bactericidal effect is unknown, it is believed to involve altering the function of the cell membrane or linking to the cell's DNA to disrupt cell function. The bactericidal action is effective against a broad spectrum of bacteria, including all of the common strains which cause infection. When these metals are used in the minute concentrations required to kill or stem the growth of bacteria, they do not have any detrimental effect on normal mammalian cells.

Silver is used routinely in antibacterial salves, such as silver sulfadiazine, and has also been used in clinical trials to coat gauze for burn dressings. Medical devices, such as catheters, with silver impregnated in a soluble collagen or polymer coating are also known. After these catheters are placed, the coating slowly dissolves and the silver is released over time into the environment. The infection rates with these products are reported to be two to four times lower than standard catheters.

One catheter that uses silver as an antibacterial agent has had only limited success because the device, consisting of a silver impregnated collagen cuff which is inserted just below the skin, is difficult to place correctly. The cuff is also expensive, increasing the cost of a central venous catheter almost three-fold. Other catheters for reducing infection rates use well known approaches, most of them varying only in the type and solubility of the silver or silver-alloy coating.

Many of the prior art catheters that use oligodynamic metals as bacteriostats fail to adequately prevent infection for one or more of the following reasons: 1) Silver released from soluble coatings is not always in the same charge state and often is not charged at all, therefore its bactericidal potential is not optimized; 2) With soluble-coated catheters, once the coating dissolves, usually over about two weeks there is no further antibacterial protection; 3) A non-soluble silver, silver alloy or silver-oxide coating can prevent colonization of the catheter to a limited extent, but the oligodynamic metal is not released into the surrounding fluid or tissue; 4) Due to the substantial change in the catheter placement procedure, the use of these catheters requires additional personnel training; and 5) Although infection can enter the body through either the interior or the exterior of the catheter, not all catheters provide both interior and exterior protection. Furthermore, despite the capability of silver-alloy coated devices to produce a two to four fold reduction in bacterial colonization, their high cost greatly detracts from their modest capabilities.

Research from the 1970's onward has been directed toward improving the antibacterial effects of oligodynamic metals by electrically injecting the metal ions into solution. This process, known as oligodynamic iontophoresis, is capable of reducing bacterial colonization fifteen to one-hundred fold. Iontophoresis describes the movement of ions in a conductive fluid under the influence of low-strength electric fields, and in this context refers to the forcing of ions into a conductive fluid environment using minute electric currents. For example, if two electrodes made of a metal, such as silver, are introduced into a conductive medium, such as saline, blood or urine, and an electrical potential is applied across the electrodes, silver ions are driven into solution creating an enhanced bactericidal effect. The current required to safely drive a sufficient amount of silver ions into solution to control infection is in the range of 1 to 400 microAmperes. This current range does not cause localized cell necrosis and it is below the sensory or pain threshold.

Despite its great potential, the oligodynamic iontophoresis phenomenon has found limited use in conjunction with medical devices, although urological or Foley catheters have progressed to animal experiments. With respect to Foley catheters, researchers have identified several deficiencies in prior art devices. Foremost is that the electrodes used to force ions into solution wear out, or corrode, at the interface between air and the conductive medium. This problem probably also arises in blood or saline environments as well as urine. Other significant drawbacks with prior art iontophoretic devices include bulky, current-controlled power sources required for driving the electrodes; electrode configurations that do not protect both the outside and the inside of the catheter; and manufacturing processes that are labor intensive.

An example of an infection control catheter that uses separate electrodes on the catheter and an external power supply to drive ions into solution is U.S. Pat. No. 4,411,648 to Davis. Other prior art oligodynamic iontophoresis devices do not use external power supplies. For example, U.S. Pat. No. 4,886,505 to Haynes, teaches placing two metals in direct physical contact to produce electrical currents. The currents produced, however, are likely to be too large to be safely used and possibly will alter the pH of the environment. In German Patent Document DE 3,830,359, two dissimilar metal powders not in electrical contact with each other are embedded in a nonconductive catheter material, such as electrically insulating polymers. Because of the separation of dissimilar metals by an insulator, it is not likely that there is any iontophoresis effect in this device as a result of a potential being created by the dissimilar metals, except for the possibility of when a biofilm forms on the catheter surface to complete the circuit. Were an electrical circuit to be formed in this manner, the current density would not be regulated or predictable, and the current produced therefore could be either too high to be safe or too low to be effective.

An oligodynamic iontophoresis catheter which uses the properties of metals to generate a current and to form an ion barrier for killing bacteria at a localized body entry is disclosed in U.S. Pat. No. 4,569,673 to Tesi. Tesi teaches placing a strip of an oligodynamic metal on a nonconductive substrate. The oligodynamic metal acts as a sacrificial galvanic anode and gives off ions when placed in conductive contact with a dissimilar metal by placing the catheter in an electrolytic solution. Because the conductivity and pH of urine, for example, varies over time within the same person, as well as from individual to individual, it would be extremely difficult to achieve a specific current density at a given time with any precision or predictability. Additionally, the Tesi device only provides localized infection control.

Thus, none of these devices fulfill the promise held out by oligodynamic iontophoresis for reducing infection in long-term indwelling medical devices.

SUMMARY OF THE INVENTION

The present invention provides an iontophoretic structure for a medical device that reduces the risk of infection associated with prolonged medical device implantation in the body. Specifically, the invention is directed toward meeting performance goals of general antibacterial effectiveness; minimal electrode corrosion; precise control of electrical current; portability of the current source; and ease of manufacture. These performance requirements can be readily addressed by a number of embodiments in which a controlled electrical current drives oligodynamic metal ions into solution to kill bacteria on and near the iontophoretic structure.

In one embodiment, an iontophoretic structure includes an iontophoretic material and a covering layer that covers at least a portion of the iontophoretic material. The covering layer can be chemically bonded, mechanically attached, or merged with the iontophoretic material. The iontophoretic structure can include an iontophoretic composite material, layered iontophoretic structures, or bodies overcoated with selected materials to create an iontophoretic effect.

The covering layer, which can be permeable, can include or comprise a hydrophilic substance, a blood thinner, or a non-iontophoretic polymer. In other embodiments, the iontophoretic structure further includes a coating covering at least a portion of the permeable covering layer. The coating can include a biodegradable material or a soluble material and a chemical or a biological agent that is liberated from the coating when the biodegradable material degrades or dissolves.

In another embodiment of the invention, an iontophoretic structure includes a permeable base material for a medical device that is integrated with iontophoretic bodies or structures.

BRIEF DESCRIPTION OF THE DRAWINGS

The invention will be more fully understood from the following detailed description taken in conjunction with the accompanying drawings in which.

DETAILED DESCRIPTION OF THE INVENTION

Iontophoretic structures in accordance with the invention may be divided into two categories: a composite material used to coat a medical device, or a plurality of discrete layered electrodes placed on the medical device, both of which categories are disclosed hereinbelow. The medical device can be a short-term, long-term, or permanent implant and includes such devices as: urinary catheters, vascular access catheters and introducer sheaths, fluid introduction tubing and fittings such as intravenous tubing, urinary drainage bags and tubing, chest drainage tubes, infusion pumps, pacing leads, tracheotomy tubes, ventilation tubes, prosthetic joints, heart valves, wound dressings, orthopedic pins or plates, or any other medical device used in an environment or application where anti-bacterial properties are a consideration. However, because urinary catheters are an especially attractive application for the iontophoretic structures, the ensuing detailed description is directed thereto.

Figure 1:
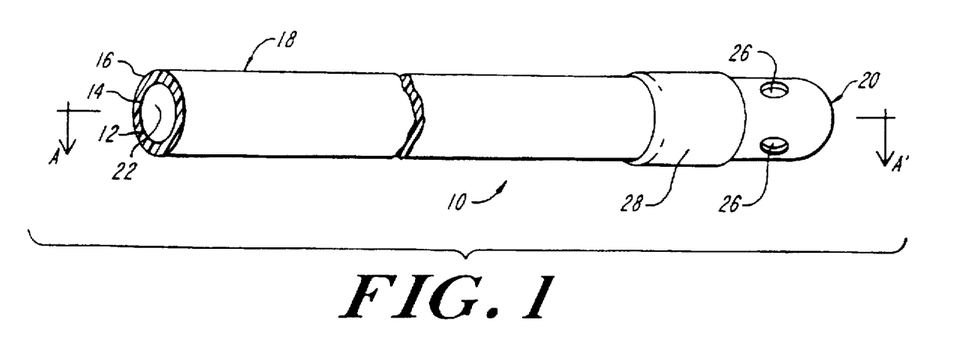
FIG. 1 is a perspective view of an iontophoresis catheter incorporating a composite material comprising metal powders in a conductive elastomeric matrix.

With respect to the first category of iontophoretic structure for a medical device, FIG. 1 illustrates an exemplary iontophoresis catheter 10 that uses the composite material approach to kill bacteria. The iontophoresis catheter 10 is substantially identical to a normal or non-infection controlling catheter in that it is a hollow flexible tube comprising an elastomeric wall 12 having an inner surface 14 and an outer surface 16, a proximal end 18, and a distal end 20. The generally cylindrical inner surface 14 defines a lumen 22 for the passage of fluid. Both the proximal end 18 and the distal end 20 are provided with one or more openings 26 to allow the fluid to be introduced or evacuated from the lumen 22. The distal end 20 is shaped to facilitate insertion or placement of the iontophoresis catheter 10 into the body. The iontophoresis catheter 10 may also be fitted with a retention device 28, such as a balloon fitting, to prevent unintentional withdrawal of the iontophoresis catheter 10 from the body.

Figure 2:
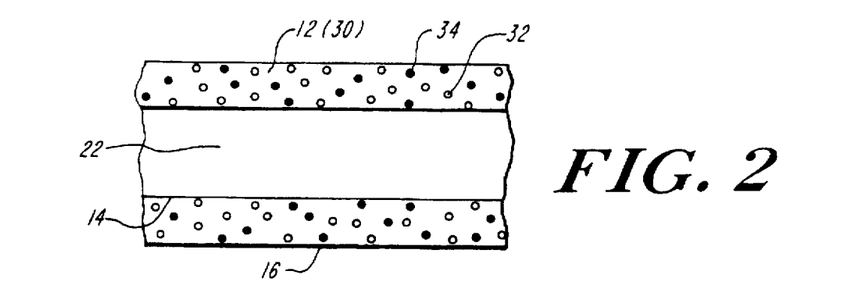
FIG. 2 is a partial sectional view of the iontophoresis catheter of FIG. 1.

FIG. 2 is a partial sectional view of the iontophoresis catheter 10 of FIG. 1, taken along the line A-A', that depicts details of a composite material comprising galvanic materials, such as metal powders, in a conductive elastomeric matrix 30 that distinguishes the iontophoresis catheter 10 from prior art catheters. The wall 12 of the catheter comprises the conductive base material 30, and a first and a second dissimilar metal powder, 32 and 34 respectively. The base material 30 is a conductive polymer similar to that used in static-proof bags for packaging charge-sensitive electronics in which the conductivity (resistivity) is controlled to a predetermined value by its composition. Exemplary conductive polymers can be made from polymers including polyvinyl, polyester, polyethylene, or a naturally conductive polyvinylidene fluoride. When loaded with carbon or other conductive fillers, for example, these polymers can be made conductive and thereby used as the base material 30 for an iontophoresis catheter 10. Exemplary first and second metal powder combinations having an electrochemical half-cell potential difference include silver and gold, silver and copper, or silver and platinum mixed into the polymer at very low volume concentrations prior to extrusion fabrication of the composite catheter 10. Although these exemplary powders are relatively expensive, they are used in such minute quantities that their use does not adversely impact overall cost of the iontophoresis catheter 10.

For catheter applications in which the elastomeric wall 12 is extruded, it is feasible to make the entire wall 12 from the composite material 30, 32, 34. However, Foley catheters which are typically made of latex and/or silicone rubber are not extruded, but are generally dip-cast, and finish-coating in a final dip is a natural processing step in their manufacture. Therefore, the iontophoresis catheter 10 can be made by finish-coating it with the composite material 30, 32, 34. Since rubber is generally inferior to plastic in terms of infection rates, overcoating with a castable plastic is advantageous in and of itself.

When the composite catheter 10 is placed in contact with or immersed in a fluid that is electrolytic, such as saline, blood, drug preparations, or urine, the first and second metal powders 32, 34 become an array of small batteries. Specifically, each powdered metal granule embedded in the base material 30 that makes contact with the electrolytic fluid 24 becomes either an anode or a cathode, depending on the particular metals chosen as the first and second metal powders 32, 34.

Figure 3:
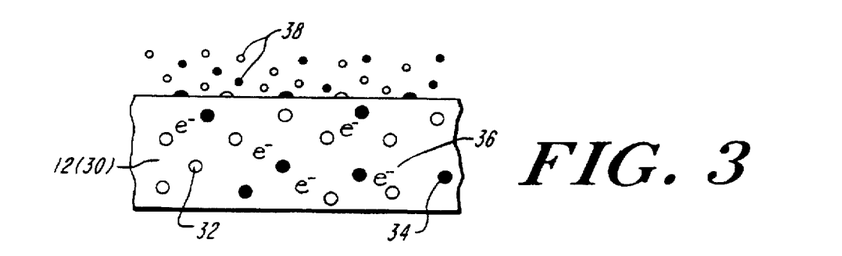
FIG. 3 is a depiction of the iontophoresis effect created by the composite material in the catheter of FIG. 1.

Referring to FIG. 3, a depiction of the iontophoresis effect created by the composite material 30, 32, 34 in the catheter of FIG. 2 is shown. The first and second metal powders 32, 34 act as electrodes and create a voltage potential therebetween, whereby electrons 36 migrate through the base material 30 and generate an electric current. Metal ions 38 are thus driven into the conductive fluid 24 by iontophoresis. The electric current is regulated by the quantity and nature of metal powder 32, 34 embedded in the base material 30 and by the conductivity of the base material 30. These factors are adjusted so that the current and ultimate metal ion densities are in an efficacious and safe range by use of the following formula:

$$I\left(\frac{AMP}{CM^2}\right) = \frac{V}{4r\rho} \ln\left[\frac{L^{-2/3}}{L^{-2/3}-1}\right]$$

wherein:

"I" is the total average current per unit surface area (amperes per cm$^2$);

"$\rho$" is the volume resistivity of the conductive base material 30 (ohm-cm);

"r" is the average metal powder granule radius (cm);

"VI" is the voltage produced by the two dissimilar metals powders 32, 34 in the electrolytic fluid; and "L" is the metal powder volume loading of the base material as a fraction (ie 0–1).

With respect to the above formula, the metal powders are assumed to be of the same granule size and of the same volume loading. In practice, they do not have to be the same size and volume loading. To achieve a current density between $10^{-8}$ to $10^{-6}$ Amperes per mm$^2$, which is the desired range to be bacteriostatic or bactericidal and yet not be so high as to cause pH changes or other deleterious mammalian cell reactions, the following exemplary values can be used in the above equation to define the composite material specifications:

V=0.12 volts (for silver and gold in an NaCl electrolyte);
r=$10^{-3}$ cm;
$\rho$=1.5×$10^6$ to 1.5×$10^4$ ohm-cm; and
L=0.01.

An iontophoresis catheter 10 incorporating the above described composite material has numerous advantages over the prior art with respect to effectiveness, controllability, and ease of use. Foremost, bacterial potency is maximized because metal is guaranteed to go into solution as ions, thus producing a minimum ten-fold reduction in bacterial colonization rate. Also, the iontophoresis catheter 10 does not need an external current source or controller because the iontophoresis current is self-generating and self-regulating. Furthermore, because the metal powders 32, 34 (electrodes) are dispersed through the base material 30, and because the current level is very low, the electrodes are functional for months of use. There is also no place in the circuit where corrosion of the electrodes at the air/electrolyte interface can cause the entire catheter to become non-functional with regard to its infection resistance. Finally, there is no change in procedure for placing or maintaining the iontophoresis catheter 10 because it is in many ways virtually identical to existing non-infection control devices in size and shape.

Figure 4:
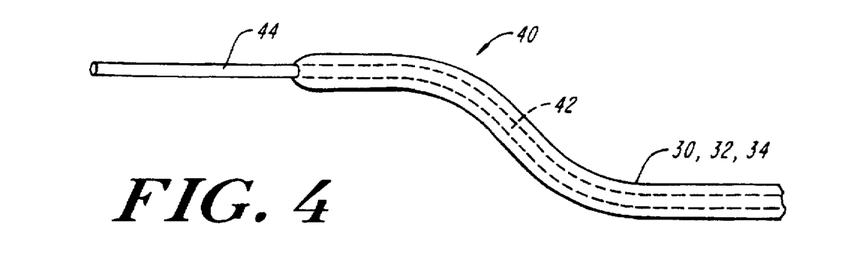
FIG. 4 is a perspective view of a pacing lead coated with the composite material of FIG. 1.
Figure 5:
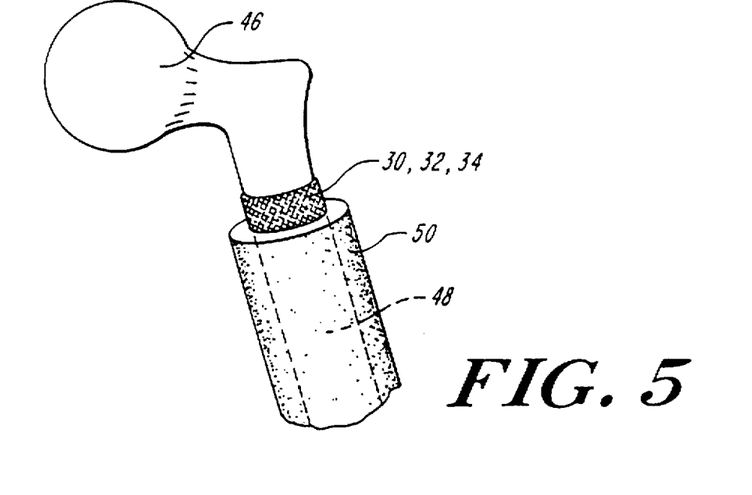
FIG. 5 is a perspective view of an artificial hip joint partially coated with the composite material of FIG. 1.
Figure 6A:
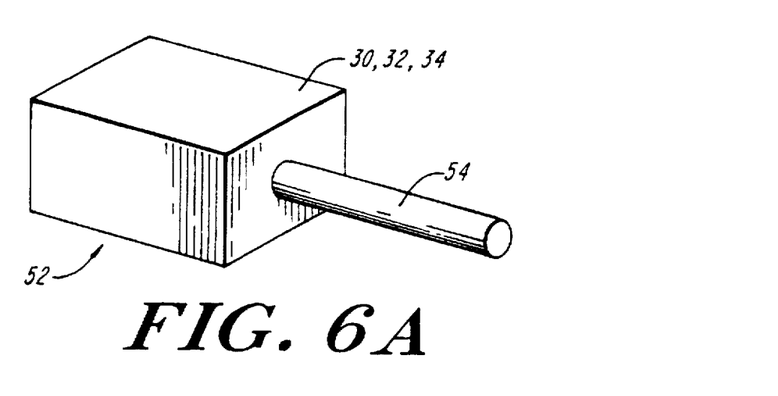
FIG. 6A is a perspective view of an infusion pump coated with the composite material of FIG. 1.

As previously discussed, the composite material approach finds ready application on numerous other medical devices where antibacterial properties are desirable. FIG. 4 is an illustration of the composite material 30, 32, 34 used to protect a pacing lead 40. The pacing lead 40 connects the heart tissue to the control and monitoring apparatus of a cardiac pacemaker (not shown) via a wire 42 and an electrode 44 in the tissue. The wire 42 is shown covered with the composite material 30, 32, 34. FIG. 5 is a depiction of the composite material 30, 32, 34 used with a prosthetic device, such as an artificial hip joint 46. The shaft 48 is shown coated with composite material 30, 32, 34 and implanted into a femur 50. FIG. 6A shows an infusion pump 52 coated with the composite material 30, 32, 34 and connected to tubing 54 which may also be coated.

Figure 6B:
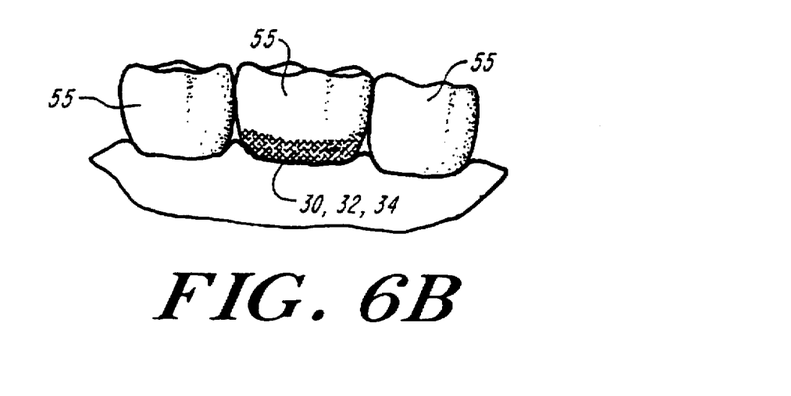
FIG. 6B is a perspective view of a tooth coated with the composite material of FIG. 1.

The composite material 30, 32, 34 can also be coated onto a natural body structure 55, such as a tooth, as illustrated in FIG. 6B. This is accomplished by painting the composite material 30, 32, 34 onto the surface to be protected while the base material 30 is in a liquified or softened state and then letting the base material 30 harden. In an alternative embodiment the base material 30 is binary adhesive, such as a catalytic, two-part, conductive epoxy mix.

Figure 7:
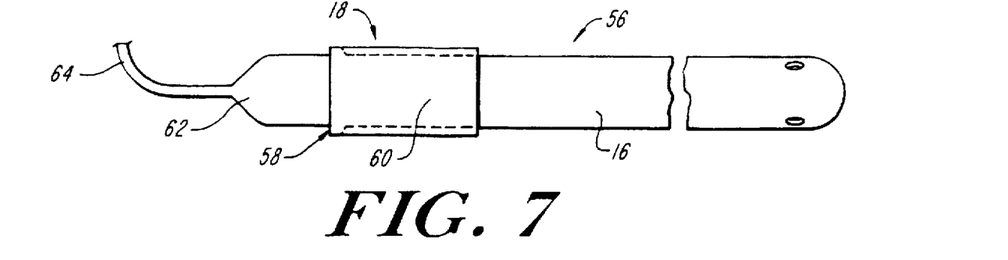
FIG. 7 is a perspective view of a catheter with an iontophoresis infection control sheath.

With further regard to catheters, a vascular access add-on device that benefits from the composite material approach for an iontophoretic structure is shown in FIG. 7, wherein an ordinary catheter 56 is shown fitted with an infection control kit 58 incorporating the composite material 30, 32, 34. The infection control kit 58 is an after-market device which includes a replaceable iontophoretic infection control sleeve 60 and an iontophoretic Luer adaptor 62 for connecting the proximal end 18 of the catheter 56 to intravenous (I.V.) tubing 64. The sleeve 60, made of or coated with the composite material 30, 32, 34 slips over the outer surface 16 of the catheter 56 to be inserted the body. The sleeve 60 covers only a short section of the catheter 56 near its proximal end 18, but is long enough to enter the body wherein moisture will activate the iontophoresis process. The sleeve 60 thus protects the catheter surface 16 from infection. The Luer adaptor 62 may also be made of or coated on the inner surface with the composite material 30, 32, 34 to protect the inner surface 14 of the catheter 56 from bacterial colonization progressing down to the catheter 56 from the inside of the I.V. tube 64. The sleeve 60 is fabricated from one of the above referenced conductive base materials 30; and the Luer adaptor 62 is made of a harder plastic, such as acrylic or polycarbonate. The sleeve 60 may be configured to accommodate a variety of catheter sizes.

Figure 8:
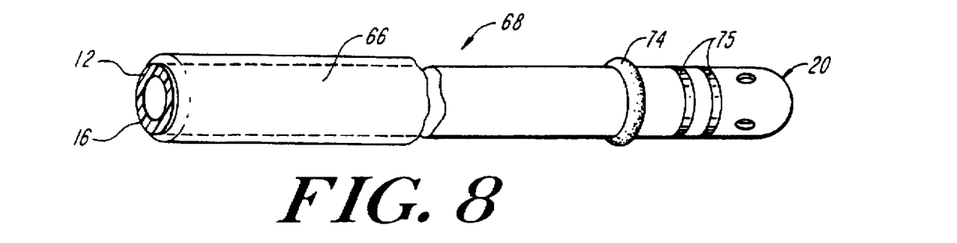
FIG. 8 is a perspective view of a catheter with an iontophoresis infection control introducer sheath.

An adaptation of the composite material sleeve 60 can also be configured as a catheter introducer sheath 66, shown in FIG. 8, for inserting pulmonary artery (Swan-Ganz or thermodilution) catheters, temporary pacing leads, etc., which may remain in place for several weeks. Under normal circumstances, an introducer sheath is left in place with the catheter which it surrounds for a portion of its length, including the region where the device penetrates the skin. Iontophoretic introducer sheaths 66 are easily manufactured with the composite material approach because they are predominantly made of polytetrafluorethylene (Teflon®), vinyl (PVC), or polyethylene (PE), materials which can be loaded with carbon or other conductive fillers or made conductive by other means known in the art and then loaded as well as the first and second metal powders 32, 34.

FIG. 8 shows the introducer sheath 66 used in conjunction with a thermodilution catheter 68. Balloon and temperature sensing elements, 74 and 75 respectively, known to those skilled in the art, are shown on the distal end 20. Because the inside of the introducer sheath 66 is in intimate contact with the outer surface 16 of the elastomeric wall 12, the composite material 30, 32, 34 of the introducer sheath 66 protects both the sheath 66 and the outer wall 12 of the thermodilution catheter 68. Like the iontophoresis catheter 10, and the catheter 56 having an iontophoresis infection control kit 58, the introducer sheath 66 is virtually identical in size, shape, and use as prior art devices.

As described with respect to FIGS. 1–8, various embodiments of the composite material category of the iontophoretic structure for a medical device have been illustrated. In composite material embodiments, the integral power source for driving oligodynamic metal ions into solution is the electromotive force created by dissimilar metal powders 32, 34 embedded in and separated from each other by the conductive base material 30 of specifically created resistivity.

Figure 9:
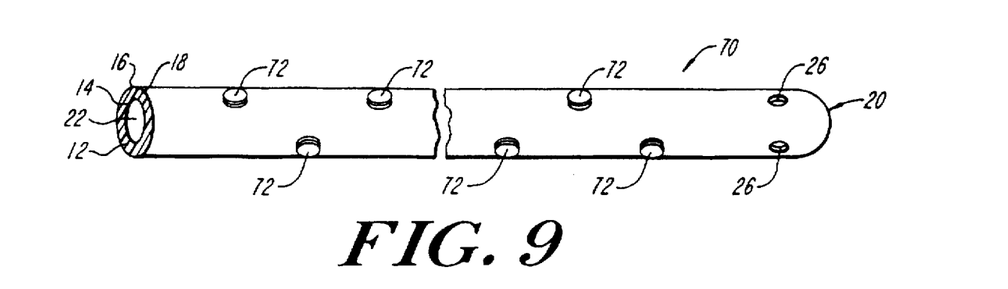
FIG. 9 is a perspective view of an iontophoresis catheter having a plurality of layered electrodes.
Figures 10, 11:
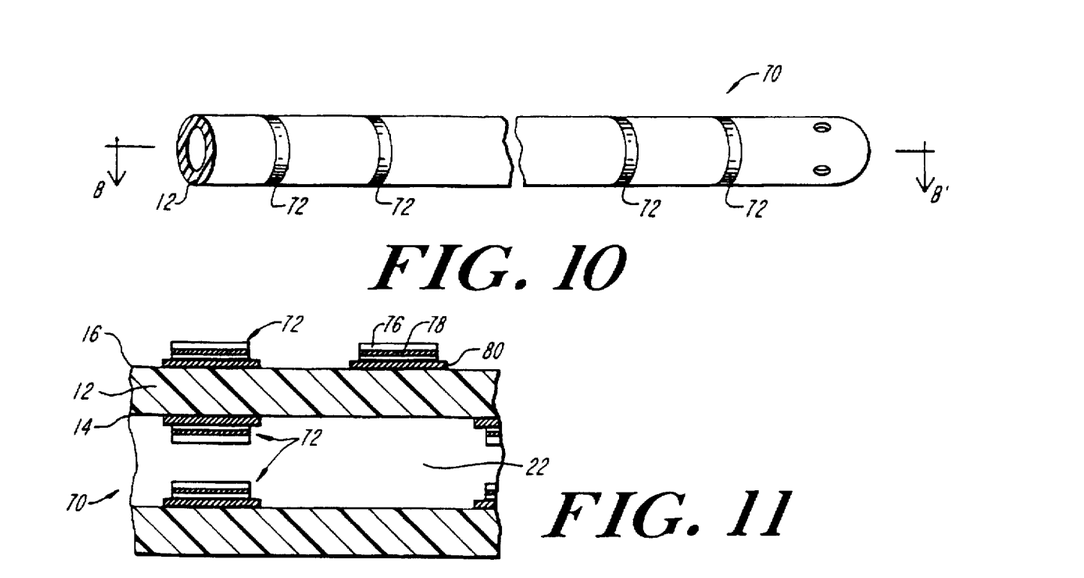
FIG. 10 is a perspective view of an alternative embodiment of an iontophoresis catheter having a plurality of layered electrodes arranged in strips.
FIG. 11 is a partial sectional view of the iontophoresis catheter of FIG. 10.

Referring now to FIGS. 9–11, a variety of embodiments of the other category of iontophoretic structure for a medical device are shown which incorporate the plurality of discrete layered structures. In these embodiments a plurality of layered structures comprise dissimilar galvanic materials separated by a resistive layer. These structures may be incorporated in the above-recited medical devices during manufacture, or adhered to the surface of the devices as an aftermarket item.

Referring to FIG. 9 a perspective view of an embodiment of an iontophoresis catheter 70 is shown, wherein the oligodynamic iontophoresis effect is achieved using a plurality of layered structures 72 on either the inner surface 14, the outer surface 16, or both of a non-conductive wall 12. The layered structures 72, while depicted in a circular configuration can be any shape, such as oval or square.

FIG. 10 depicts an alternative configuration of the iontophoresis catheter 70, wherein the plurality of layered structures 72 are bands that surround the wall 12. Alternatively, the layered structures 72 can be a plurality of longitudinal strips. The embodiments of FIGS. 9 and 10 permit selective placement of a layered structure 72 on an isolated region of the wall 12, or distribution of the layered structures 72 on the entire wall 12.

Referring to FIG. 11, a partial cross section of the iontophoresis catheter 70 of FIG. 10 along the line B-B' is shown, wherein the layered structures 72 are bands adhered to the inner surface 14 and outer surface 16 of the wall 12. Each layered electrode 72 comprises a first metal electrode 76, a resistive layer 78, and a second metal electrode 80. As with the iontophoresis catheter 10 of FIG. 1, the metals are biocompatible and form an electrical potential difference between them in an electrolytic fluid. Whereas, in the iontophoresis catheter 10 of FIG. 1 the conductive (resistive) base material 30 regulates the current flow between the first and second metals 32, 34, in this embodiment the (conductive) resistive layer 78 regulates the current flow between the dissimilar metals of the first and second electrodes 76, 80.

For the iontophoresis catheter 70 of FIGS. 9 and 10, wherein the first and second metal electrodes 76, 80 of the layered structures 72 have a 1 volt potential between them, a current density of $10^{-8}$ Amperes per $mm^2$ results if the thickness of the resistive layer 78 is approximately 10 micrometers and has a bulk conductivity of $10^{11}$ Ohm-cm and the exposed area of each of the electrodes 76, 80 in the layered structures 72 is the same. Typical combinations of metals used for the first and second metal electrodes 76, 80 generate between 0.1 to 2 Volts. Therefore, the thickness of the above described resistive layer 78 can be between 1 and 20 micrometers. Many other combinations of conductivity and thickness for the resistive layer 78 are possible to obtain the target current density.

Figure 12:
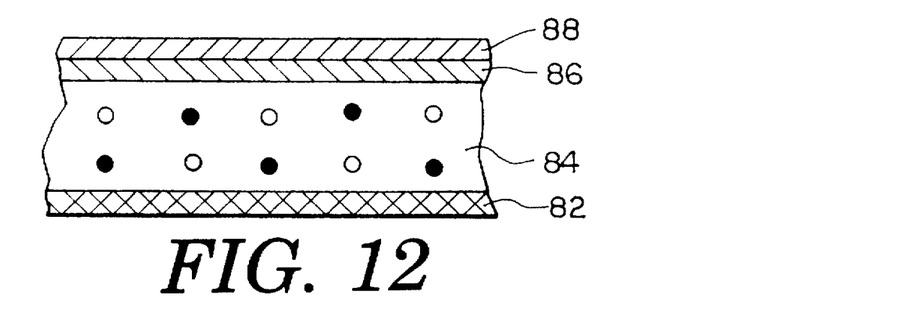
FIG. 12 is a sectional view of another embodiment of an iontophoretic structure on a device surface that includes one or more covering layers.
Figure 13:
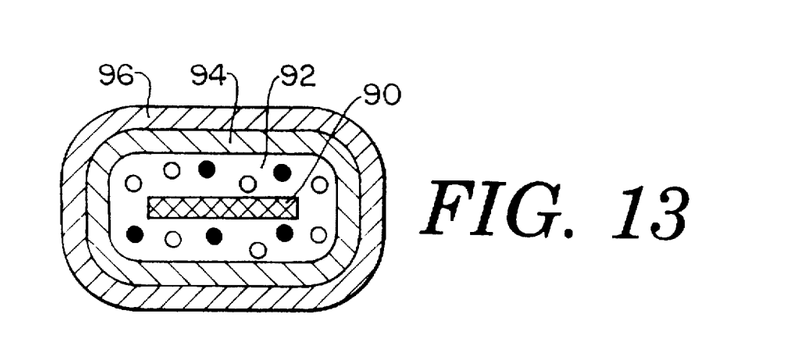
FIG. 13 is a sectional view of an iontophoretic structure that envelops a device and is itself enveloped by one or more covering layers.
Figure 14:
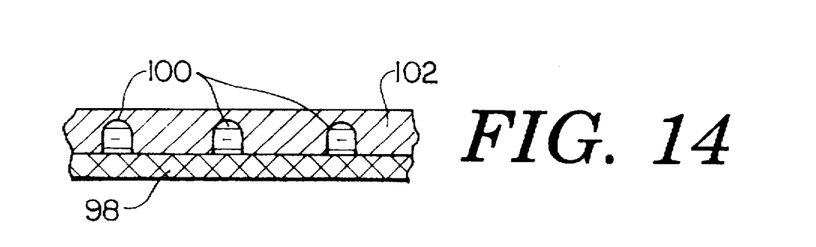
FIG. 14 is a sectional view of yet another embodiment of an iontophoretic structure on a device surface that includes a covering layer.

Although the above described iontophoretic structures and materials provide antibacterial and antifungal protection, certain configurations can be physically unstable or unsuitable for particular devices, and/or they may present an undesirable surface texture or finish for specific applications. The physical characteristics of devices incorporating or made from such structures or materials can be improved by providing them with a covering layer that stabilizes the structure and/or that provides a desired surface texture, finish, or other mechanical property. Even if the structure and properties of an iontophoretic structure or material are acceptable, it is sometimes desirable to provide supplemental benefits. As shown in FIGS. 12, 13, and 14, these goals can be accomplished in embodiments of the invention, wherein either all or a portion of an iontophoretic structure or composite material is provided with a permeable covering material that has different chemical, biological, mechanical, or physical properties from the underlying iontophoretic surface.

FIG. 12, for example, illustrates a substrate 82 that is representative of a surface portion of a medical device. The substrate 82 is covered with a material 84 that has iontophoretic properties. Although it is believed that when the material 84 includes an iontophoretic structure such as the composite material or the layered electrodes described hereinabove, a superior antibacterial effect is achieved, the material 84 can also include any other substance or structure known that creates an iontophoretic effect. Chemically bonded to, mechanically attached to, physically merged with, or merely covering an outer layer of the material 84 is a covering layer 86. The covering layer 86 is permeable or semi-permeable (collectively "permeable") to all of the ionic species necessary to cause the underlying iontophoretic material 84 to function. However, a non-permeable covering layer material that is either permanent or degradable can be applied to the iontophoretic material 84 to permanently or temporarily alter the iontophoretic effectiveness of the device across its entirety or at one or more localized regions.

The covering layer 86 can include a hydrophilic substance that improves lubricity or antithrombogenicity. The covering layer 86 can also include heparin for antithrombogenicity. To improve surface finish or to reduce the iontophoretic rate, the covering layer 86 can comprise a pure polymer. The covering layer can also comprise a different polymer from the iontophoretic materials for improved biocompatability, or wear and fatigue properties. In an exemplary embodiment, a polyurethane based iontophoretic material is coated with silicone. In another embodiment, a silicone based iontophoretic material is coated with polyurethane.

Also as shown in FIG. 12, the covering layer 86 can be provided with a coating 88 that dissolves in its target environment or that is biodegradable to delay the onset of the iontophoretic action and/or to reduce the iontophoretic effect. Furthermore, the coating 88 can include chemicals or biologicals that provide other effects of interest and that are released when the coating dissolves or degrades. With respect to any of the materials selected for the covering layer 86 or the coating 88, a coloring agent or pigmentation can be added for aesthetic reasons and to identify device function or material properties.

The coating 88 can be provided, as shown in FIG. 12, as a layer that is separate and distinct from the permeable covering layer 86. Alternatively, the materials of the coating 88 and the covering layer 86 can be commingled to provide a single layer. In an exemplary embodiment a device is provided with a permeable, biodegradable layer or covering that has a lubricous surface for ease of placement of the device.

FIG. 13 illustrates yet another embodiment of an iontophoretic medical device, wherein a substrate 90 is completely enveloped by a material 92 that has iontophoretic properties as described above with respect to FIG. 12. Chemically bonded to, mechanically attached to, or physically merged with an outer layer of the material 92 is a covering layer 94, as described above with respect to FIG. 12, that completely envelops the material 92. The covering layer 94 can be provided with a coating 96 that dissolves in its target environment or that is biodegradable, as set forth above with respect to the coating 88 of FIG. 12. As set forth above, the covering layer 94 and the coating 96 can be one and the same layer.

FIG. 14 illustrates how the surface properties of a medical device including an iontophoretic structure or composite material can be improved when the medical device or the iontophoretic structure or material has an irregular, non-uniform, or rough surface, or comprises a number of discrete structures on the surface of a medical device. More specifically, FIG. 14 depicts a substrate 98, representative of the surface of a medical device, that is covered with layered structures 100, as shown with respect to FIGS. 9–11. The height of the layered structures 100 is exaggerated in FIG. 14 for illustrative purposes. A covering layer 102 is provided over the substrate 98 and the layered structures 100.

Figure 15:
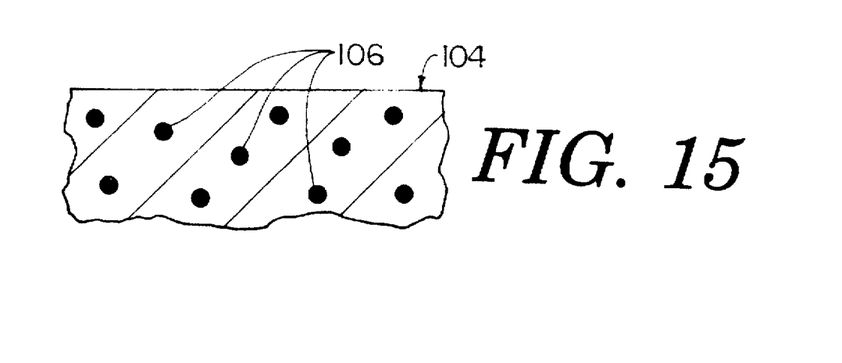
FIG. 15 illustrates a medical device that incorporates iontophoretic structures.

In addition to being partially coated or completely enveloped by iontophoretic material or structures, all or a portion of a medical device can be integrated with, impregnated by, or fabricated from an iontophoretic material. In some cases, it is desirable to leave a medical device base material in an unaltered state. In those cases, discrete iontophoretic structures can be incorporated as a composite into the base material as depicted in FIG. 15. More particularly, FIG. 15 illustrates a portion of a medical device 104 comprising a base material, wherein discrete iontophoretic structures 106 or material bodies are mixed with, dispersed through, or otherwise made integral with the base material of the medical device. The medical device 104, which can be of any shape or size, includes a base material that must be permeable or semi-permeable to the ion species necessary to cause the integral iontophoretic structure or material to function as described above. Although a medical device can be made entirely of the iontophoretic composite material, the configuration illustrated in FIG. 15 is intended for applications wherein the base material has certain desirable properties which one may wish to retain. It should be noted that the base material does not need to be conductive.

In an exemplary embodiment, particulates of an iontophoretic composite material or multiple layered structures, as described above, are embedded in a base polymer. In another embodiment, the iontophoretic material includes bodies made or coated with one of the dissimilar metals that are partially or completely overcoated with the second dissimilar metal, and the bodies are embedded in a base material. In yet another embodiment the iontophoretic material includes platinum bodies or platinum coated bodies that are partially or completely overcoated with silver and embedded in a base material. Alternatively, silver bodies or silver coated bodies that are partially or completely overcoated with platinum are embedded in a base material. The base material can be optically clear.

Although the invention has been shown and described with respect to exemplary embodiments thereof, various other changes, omissions and additions in form and detail thereof may be made therein without departing from the spirit and scope of the invention.

What is claimed is:

1. An iontophoretic structure comprising:
   an iontophoretic material comprising one of an iontophoretic composite material and a layered iontophoretic structure; and
   a covering layer disposed on a surface portion of the iontophoretic material.

2. The iontophoretic structure of claim 1, wherein said covering layer is chemically bonded to said iontophoretic material.

3. The iontophoretic structure of claim 1, wherein said covering layer is mechanically attached to said iontophoretic material.

4. The iontophoretic structure of claim 1, wherein said covering layer is merged with said iontophoretic material.

5. The iontophoretic structure of claim 1, wherein said covering layer is permeable.

6. The iontophoretic structure of claim 5, wherein said covering layer includes a hydrophilic substance.

7. The iontophoretic structure of claim 5, wherein said covering layer includes one of a blood thinner and an anticoagulant.

8. The iontophoretic structure of claim 5, wherein said covering layer includes a polymer.

9. The iontophoretic structure of claim 5, further including a coating covering at least of portion of said permeable covering layer.

10. The iontophoretic structure of claim 9, wherein said coating includes a biodegradable material.

11. The iontophoretic structure of claim 10, wherein said coating includes one of a chemical and a biological agent that is liberated from said coating when said biodegradable material degrades.

12. The iontophoretic structure of claim 9, wherein said coating includes a liquid soluble material.

13. The iontophoretic structure of claim 12, wherein said coating includes one of a chemical and a biological agent that is liberated from said coating when said liquid soluble material dissolves.

14. The iontophoretic structure of claim 9, wherein said coating further includes pigmentation.

15. The iontophoretic structure of claim 9, wherein said covering layer and said coating are merged to provide a single layer that covers at least a portion of said iontophoretic material.

16. The iontophoretic structure of claim 5, further comprising a substrate that is at least partially covered by said iontophoretic material.

17. The iontophoretic structure of claim 5, further comprising a substrate that is completely enveloped by said iontophoretic material.

18. The iontophoretic structure of claim 5, wherein said iontophoretic structure has an irregular surface and said covering layer imparts a smooth surface to said iontophoretic structure.

19. The iontophoretic structure of claim 1, wherein said covering layer includes a biodegradable material.

20. The iontophoretic structure of claim 19, wherein said covering layer includes one of a chemical and a biological agent that is liberated from said coating when said biodegradable material degrades.

21. The iontophoretic structure of claim 1, wherein said covering layer includes a liquid soluble material.

22. The iontophoretic structure of claim 21, wherein said covering layer includes one of a chemical and a biological agent that is liberated from said coating when said liquid soluble material dissolves.

23. The iontophoretic structure of claim 1, wherein said covering layer further includes pigmentation.

24. The iontophoretic structure of claim 1, wherein said covering layer imparts lubricity to said iontophoretic structure.

25. The iontophoretic structure of claim 1, wherein said covering layer is wear and fatigue resistant.

* * * * *

UNITED STATES PATENT AND TRADEMARK OFFICE
CERTIFICATE OF CORRECTION

PATENT NO : 5,759,564
DATED : June 2, 1998
INVENTOR(S): Fredric L. Milder et al.

It is certified that error appears in the above-identified patent and that said Letters Patent is hereby corrected as shown below:

On the title page, Inventors: delete "Frederic" and insert --Fredric--.

At Column 5, Line 49, delete "VI" and insert --V--.

Signed and Sealed this

Second Day of February, 1999

Attest:

Attesting Officer

*Acting Commissioner of Patents and Trademarks*